United States Patent
Nakamura

(10) Patent No.: US 6,211,396 B1
(45) Date of Patent: Apr. 3, 2001

(54) PROCESS FOR PRODUCING HALOGEN-CONTAINING PHOSPHATE ESTER

(75) Inventor: Shin Nakamura, Aichi (JP)

(73) Assignee: Daihachi Chemical Industry Co., Ltd. (JP)

( * ) Notice: Subject to any disclaimer, the term of this patent is extended or adjusted under 35 U.S.C. 154(b) by 0 days.

(21) Appl. No.: 09/509,419

(22) PCT Filed: Jul. 13, 1999

(86) PCT No.: PCT/JP99/03777

§ 371 Date: Jun. 5, 2000

§ 102(e) Date: Jun. 5, 2000

(87) PCT Pub. No.: WO00/06584

PCT Pub. Date: Feb. 10, 2000

(30) Foreign Application Priority Data

Jul. 27, 1998 (JP) .................................................. 10-211628

(51) Int. Cl.$^7$ ....................................................... C07F 9/09
(52) U.S. Cl. ............................... 558/92; 558/94; 558/203
(58) Field of Search ................................. 558/92, 94, 203

(56) References Cited

FOREIGN PATENT DOCUMENTS

| 03193793 | 8/1991 | (JP) . |
| 07275891 | 10/1995 | (JP) . |
| 08024872 | 1/1996 | (JP) . |
| 09052099 | 2/1997 | (JP) . |

*Primary Examiner*—Michael G. Ambrose
(74) *Attorney, Agent, or Firm*—Fish & Neave; James F. Haley, Jr.; Elinor K. Shin

(57) ABSTRACT

A process for producing a halogen-containing phosphate ester includes the steps of: (i) reacting a phosphorus halide selected from the group consisting of phosphorus oxyhalides and phosphorus pentahalides with a halogen-containing hydroxy compound to obtain a reaction mixture including a halogen-containing phosphate ester, (ii) purifying the halogen-containing phosphate ester by adding an aqueous medium selected from the group consisting of water, neutral aqueous solutions, acidic aqueous solutions and basic aqueous solutions to the reaction mixture to crystallize the halogen-containing phosphate ester, and (iii) distilling waste water from the purification step.

12 Claims, No Drawings

PROCESS FOR PRODUCING HALOGEN-CONTAINING PHOSPHATE ESTER

TECHNICAL FIELD

The present invention relates to a process for producing a halogen-containing phosphate ester which is produced in various areas such as chemical and pharmaceutical industries. More specifically, the present invention relates to a clean process for producing a halogen-containing phosphate ester in which deleterious waste water generated during production of the halogen-containing phosphate ester is cleaned.

BACKGROUND ART

Halogen-containing phosphate esters are compounds widely used in various areas including chemical and pharmaceutical industries as resin additives such as flame retardants and plasticizers, intermediates for medicaments or pesticides and the like. When those halogen-containing phosphate esters which are solid at room temperature, among others, are produced, the products are effectively purified by the crystallization processes used to increase the quality of the products. However, when phosphate esters are produced by using crystallization processes, waste water which contains phosphorus-containing organic pollutants is generally generated.

Waste water from chemical plants and organic sewage such as drainage generally contain COD materials and phosphorus. The COD material refers to any organic material which indicates certain COD (i.e., chemical oxygen demand) in an aqueous solution. Since phosphorus has a considerable effect on the environment, effective removal of phosphorus from the waste water or organic sewage is important. Biological treatment or biodegradation has been known as one of the treatment methods for the waste water and organic sewage. Japanese Laid-open Patent Publications (Kokai) Nos. 7-275891 and 8-24872 describe processes in which phosphorus-containing waste water is biologically treated in an activated sludge treatment device to remove phosphorus from the waste water.

However, it has been difficult to effectively remove phosphorus-containing organic pollutants which are generated during production of halogen-containing phosphate esters, from the waste water, by conventional biodegradation. One of the reasons for such difficulty is that the pollutants contained in the waste water from the process for producing a halogen-containing phosphate ester, unlike the waste water from a process for producing a halogen-free phosphate ester, may include halogenated organic phosphorus in addition to inorganic phosphorus. Moreover, in the case that the waste water contains additional materials such as catalyst residue and unreacted raw materials, the biodegradation is expected to become more difficult. Furthermore, such waste water may adversely affect the natural environment as well as health of neighborhood and workers dealing with the treatment. In addition, devices for the biodegradation are generally those of a very large scale which are difficult to control. Moreover, treatment of the sludge involved in the biodegradation requires high cost.

The objective of the present invention is to provide a clean and safe process for producing a halogen-containing phosphate ester without generating deleterious materials, in which pollutants, especially phosphorus, are removed from waste water generated during production of the halogen-containing phosphate ester.

DISCLOSURE OF INVENTION

In order to address the above-mentioned difficulties, the present inventors have applied a distillation procedure to the process for producing a halogen-containing phosphate ester, which includes purification by crystallization. By the use of the distillation, water is removed from an aqueous solution which contains impurities in ppm levels, so that the impurities are left as a residue and removed. Hitherto, those skilled in the art have not considered such distillation to be practical for industrial use in view of its cost and efficiency. However, the present inventors have found that organic pollutants, especially phosphorus, can be easily, effectively and almost completely removed from the waste water generated during production of a halogen-containing phosphate ester at low cost by applying the distillation procedure to the production process.

According to one aspect of the present invention, the process for producing a halogen-containing phosphate ester includes the steps of (i) reacting a phosphorus halide selected from the group consisting of phosphorus oxyhalides and phosphorus pentahalides with a halogen-containing hydroxy compound to obtain a reaction mixture including a halogen-containing phosphate ester, (ii) purifying the halogen-containing phosphate ester by adding an aqueous medium selected from the group consisting of water, neutral aqueous solutions, acidic aqueous solutions and basic aqueous solution to the reaction mixture to crystallize the halogen-containing phosphate ester, and (iii) distilling waste water from the purifying step.

In one embodiment of the invention, the melting point of the halogen-containing phosphate ester may be about 30° C. or more. The melting point of the halogen-containing phosphate ester may be preferably about 90° C. or more.

In another embodiment of the invention, the halogen-containing hydroxy compound may be a halogenated aliphatic hydroxy compound. The halogenated aliphatic hydroxy compound may be a brominated neopentyl alcohol. The brominated neopentyl alcohol may be tribromoneopentyl alcohol.

In still another embodiment of the invention, the halogen-containing phosphate ester is tris(tribromoneopentyl) phosphate.

In still another embodiment of the invention, about 0.001 to about 20 parts by weight of the aqueous medium is added to 100 parts by weight of the reaction mixture in the purification step.

In still another embodiment of the invention, prior to the step of distillation, the waste water from the purification step is subjected to separation from the halogen-containing phosphate ester by the use of a continuous centrifugal device.

In still another embodiment of the invention, the step of distillation is carried out in a continuous manner.

According to another aspect of the present invention, the process for treating waste water generated during production of a halogen-containing phosphate ester indicates the step of distilling the waste water generated during purification of a halogen-containing phosphate ester by crystallization in which an aqueous medium selected from the group consisting of water, neutral aqueous solutions, acidic aqueous solutions and basic aqueous solutions is added to a reaction mixture including the halogen-containing phosphate ester, wherein the reaction mixture is obtained by reacting a phosphorus halide selected from the group consisting of phosphorus oxyhalides and phosphorus pentahalides with a halogen-containing hydroxy compound.

Thus, the invention described herein makes possible the advantages of (1) providing a clean and safe process for producing a halogen-containing phosphate ester substantially without generating deleterious material, in which the pollutants, especially phosphorus, are removed from deleterious waste water generated during production of the halogen-containing phosphate ester.

These and other advantages of the present invention will become apparent to those skilled in the art upon reading and understanding the following detailed description.

BEST MODE FOR CARRYING OUT THE INVENTION

A halogen-containing phosphate ester produced by the process of the present invention is purified by crystallization as described below. Thus, the process of the present invention is preferably applied to production of a halogen-containing phosphate ester which is solid at room temperature. The melting point of the halogen-containing phosphate ester is preferably about 30° C. or more, more preferably about 90° C. or more, and most preferably about 120° C. or more.

Examples of the halogen-containing phosphate ester, which is solid at room temperature, produced by the process according to the present invention include, for example, tris(halogenated aliphatic) phosphates such as tris (bromoneopentyl) phosphate, tris(dibromoneopentyl) phosphate, tris(tribromoneopentyl) phosphate, tris (chloroneopentyl) phosphate, tris(dichloroneopentyl) phosphate, tris(trichloroneopentyl) phosphate, tris (iodoneopentyl) phosphate, tris(diiodoneopentyl) phosphate, tris(tri-iodoneopentyl) phosphate, tris (bromochloroneopentyl) phosphate, tris (dibromochloroneopentyl) phosphate, tris (bromodichloroneopentyl) phosphate and bis (tribromoneopentyl)(dibromoneopentyl) phosphate; tris (halogenated aryl) phosphates such as tris(chlorophenyl) phosphate, tris(dichlorophenyl) phosphate, tris (trichlorophenyl) phosphate, tris(bromophenyl) phosphate, tris(dibromophenyl) phosphate and tris(tribromophenyl) phosphate; and condensation type halogen-containing phosphate esters such as dibromoneopentylglycol bis[bis(phenyl) phosphate], ethylene glycol bis[bis(chlorophenyl) phosphate] and chlorinated bisphenol A bis[bis(phenyl) phosphate].

The process of the present invention is preferably applied to production of the tris(halogenated aliphatic) phosphates, and more preferably to production of tris (tribromoneopentyl) phosphate.

The process of the present invention is more specifically described hereinbelow.

(reaction step)

The reaction step in the process of the present invention is a step in which a phosphorus halide is reacted with a halogen-containing hydroxy compound to obtain a reaction mixture. In the reaction step, an esterification reaction of the phosphorus halide with the halogen-containing hydroxy compound proceeds to form a halogen-containing phosphate ester in the reaction mixture.

The phosphorus halide used in the process of the present invention includes phosphorus oxyhalides and phosphorus pentahalides. Examples of the phosphorus oxyhalides include phosphorus oxychloride and phosphorus oxybromide. Examples of the phosphorus pentahalides include phosphorus pentachloride and phosphorus pentabromide. Due to its cost and ease of handling, phosphorus oxychloride is preferred.

The halogen-containing hydroxy compound used in the process of the present invention includes halogenated aliphatic hydroxy compounds such as bromoneopentyl alcohol, dibromoneopentyl alcohol, tribromoneopentyl alcohol, chloroneopentyl alcohol, dichloroneopentyl alcohol, trichloroneopentyl alcohol, iodoneopentyl alcohol, diiodoneopentyl alcohol, triiodoneopentyl alcohol, bromochloroneopentyl alcohol, dibromochloroneopentyl alcohol and bromodichloroneopentyl alcohol; halogenated aromatic hydroxy compounds such as chlorophenol, dichlorophenol, trichlorophenol, bromophenol, dibromophenol and tribromophenol; and halogenated polyhydroxy compounds such as bromoneopentyl glycol, dibromoneopentyl glycol, chloroneopentyl glycol, dichloroneopentyl glocol and halogenated bisphenol A.

Use of the halogenated aliphatic hydroxy compounds is an-example to which the process of the present invention is preferably applied, since these compounds may remain in waste water at a high rate and have low biodegradability. The brominated hydroxy compounds are especially preferable, brominated neopentyl alcohols are more preferable and tribromoneopentyl alcohol is most preferable. The halogen-containing hydroxy compound may be used alone or in combination of two or more of the compounds.

Any halogen-free hydroxy compound which can react with the phosphorus halide to form an ester bond may be optionally used in combination with the halogen-containing hydroxy compounds. Examples of such halogen-free compounds include alkyl alcohols such as methanol, ethanol, propanol and octanol; alkylene glycols such as ethylene glycol and propylene glycol; aromatic monohydroxy compounds such as phenol, o-, m- or p-cresol, 2,3-, 2,4-, 2,5-, 2,6-, 3,4- or 3,5-xylenol and ethylphenol; and aromatic polyhydroxy compounds such as catechol, hydroquinone, resorcinol and bisphenol A. Also, any equivalent to the hydroxy compounds as known to those skilled in the art, for example, glycidyl-containing compounds such as ethylene oxide, propylene oxide and epichlorohydrin may be used in combination with the halogen-containing hydroxy compound.

According to the present invention, the halogen-containing phosphate ester is obtained by reacting the phosphorus halide with the halogen-containing hydroxy compound, and optionally the halogen-free hydroxy compound and the like, in the presence or absence of suitable organic solvents and/or catalysts under the suitable reaction conditions including temperature, time period and pressure.

According to the present invention, any organic solvent may be used as long as it may dissolve both starting materials and reaction products, it has a boiling point over the reaction temperature, and it is inert for the reaction. Such organic solvents are usually immiscible with water; examples of such solvents include nonpolar aromatic solvents such as benzene, toluene, xylene, isopropylbenzene, chlorobenzene and dichlorobenzene.

The catalysts, which may be used in the process of the present invention, include Lewis acids such as aluminum chloride, magnesium chloride, zinc chloride, ferric chloride and stannic chloride; and Broensted acids such as sulfuric acid and p-toluenesulfonic acid. Lewis acids are preferably used as they generally have higher catalytic activity. In general, about 0.1 to about 2.0 parts by weight of the catalysts, if any, are preferably used to 100 parts by weight of the phosphorus halide.

According to the present invention, the esterification reaction in the reaction step is preferably carried out under the atmospheric pressure or reduced pressure such as about 10 to about 20 Torr, generally in the absence of water.

The esterification reaction is generally carried out at a reaction temperature ranging about 20 to about 220° C. and preferably from 120 to about 220° C. The reaction temperature may be appropriately selected depending on specific esters to be obtained.

The time period of the esterification reaction may vary depending on specific starting materials and amounts to be used. The reaction period within about 1 to about 10 hours is preferred for a practical industrial process. Many of the halogen-containing phosphate esters tend to develop color during their production. Thus, relatively short heating time in the reaction step is preferable.

(purification step)

The purification step in the process of the present invention is a step in which small or minimum amount of aqueous medium is added to the reaction mixture obtained from the above-mentioned reaction step to crystallize the halogen-containing phosphate ester of interest.

The reaction mixture obtained in the reaction step contains the halogen-containing phosphate ester which is the sought reaction product. The reaction mixture may also contain unreacted starting materials, by-products and degradation products thereof.

The aqueous medium to be added to the reaction mixture includes water, neutral aqueous solutions, acidic aqueous solutions or basic aqueous solutions.

The neutral aqueous solutions to be used as the aqueous medium may be an aqueous solution of neutral salts such as sodium chloride, sodium sulfate and potassium chloride. The acidic solutions may be an aqueous solution of inorganic or organic acids such as hydrochloric acid, sulfuric acid, acetic acid, oxalic acid, nitric acid and phosphoric acid, or acidic salts. The basic aqueous solutions may be an aqueous solution of lithium hydroxide, sodium hydroxide, potassium hydroxide, lithium carbonate, sodium carbonate, potassium carbonate, ammonia and the like.

The amount of the aqueous medium to be added to the reaction mixture is appropriately selected depending upon kinds and amounts of the solvent used in the reaction step and kind of the product to be crystallized, i.e., the halogen-containing phosphate ester. In any case, it is preferable to use the minimum amount of the aqueous medium sufficient to achieve crystallization of the product. Typically about 0.001 to about 20 parts by weight, preferably about 0.01 to about 10 parts by weight, and more preferably about 1 to about 5 parts by weight of the aqueous medium is added to 100 parts by weight of the reaction mixture. The aqueous medium less than about 0.001 part by weight or more than about 20 parts by weight may also be used so long as crystallization of the product is achieved. However, the amount of the aqueous medium is preferably as small as possible in view of the step of distillation discussed below.

The product may be crystallized as a solid by adding the aqueous medium to the reaction mixture and cooling the mixture. Prior to the distillation step described below, the solid components, the waste water and the waste organic solvents may be separated from each other by any separation procedure such as filtration and centrifugation. Preferably, the separation is carried out by the use of a continuous centrifugal device. The contamination of the halogen-containing phosphate ester into the waste water (and the waste organic solvent) may be minimized by using the continuous centrifugal device. As a result, the distillation step may be carried out more efficiently.

As the continuous centrifugal device, commercially available devices such as High-Speed Decanter (Tanabe Willtec Inc.) may be used. The solid components, the waste water and the waste organic solvents can be separated in one step by using a three-phase separation type continuous centrifugal device. Alternatively, the solid components may be first separated from the waste water and the waste organic solvents (i.e., two-phase separation) followed by separating the waste water and the waste organic solvents by procedures such as separation and filtration. The solid components thus obtained are optionally washed with water and/or alcohol, and dried to give a purified halogen-containing phosphate ester product. The separated waste organic solvents may be recycled by any procedure such as those described below.

(distillation step)

The waste water generated from the above-mentioned purification step is an aqueous solution in which pollutants such as by-products, unreacted starting materials and degradation products thereof are contained in the aqueous medium which has been added in the purification step. The waste water may be distilled by any distillation device to remove the pollutants from the waste water so that the waste water is cleaned. In general, the latent heat of vaporization of water is much higher than that of organic solvents. Therefore, in the distillation process for water, higher energy is generally needed to distill the water and recover the distillate. According to the process of the present invention, since a small amount of the aqueous medium is added in the purification step, only a small amount of waste water to be subjected to the distillation operation is generated. Therefore, according to the present invention, the waste water can be distilled in relatively short time at low cost with relatively simple equipment.

Distillation devices are generally classified into batch distillation devices and continuous distillation devices. According to the process of the present invention, any distillation device known to those skilled in the art may be used. The distillation device may be appropriately selected from various distillation and evaporation devices, for example those described in Kagaku Kogaku Binran, 4th ed. (Maruzen) or Kagaku Kogaku Jiten, 3rd ed. (Maruzen), in consideration the nature of the waste water, ability of the device, treatment cost and the like.

In view of efficiency of the production, it is preferred to conduct the reaction step and purification step continuously in one apparatus, followed by separating the waste water from the solid components and sending the separated water to another apparatus which is used solely as the distillation device. In view of distillation efficiency and ability for removal of pollutants, continuous distillation devices are preferred rather than batch distillation devices. However, the same reaction container used in the reaction step may also be used as a device for the subsequent distillation step as it is, so that a batch distillation may be carried out subsequent to the reaction step.

In the case when COD material, such as a halogen-containing hydroxy compound, contained in the waste water has a boiling point lower than that of water, or when a higher treatment rate is desired, thin layer distillation, among other continuous distillation devices, is preferable and industrially advantageous.

Examples of suitable thin layer distillation devices include commercially available devices such as Rotary Thin Layer Distillation Device (Kansai Chemical Engineering), WFE Thin Layer Distillator (Shinko Pantec Co. Ltd.) and Shell & Tube Heat Exchanger (Tokai Carbon CO., Ltd.).

In the case when COD material in the waste water is solid at room temperature, or when the waste water contains metals in forms such as catalyst residue and salts formed during the reaction step, it is preferred to use a spray drier such as those described in Kagaku Kogaku Binran, 4th ed.

(supra), p.746–754; Kagaku Kogaku Jiten, 3rd ed. (supra), p. 499; and Japanese Laid-open Patent Publication (Kokai) No. 48-41996, since the separated solid can be easily recovered by using such a spray drier. A vacuum spray drier is characterized in that the sample to be dried is sprayed into a powder collection container or a separation bath via a heating tube at high speed. The vacuum spray drier is small in size so that it serves to save space in a plant, and has good operability and high treatment efficiency (see, for example, Japanese Laid-open Patent Publication (Kokai) Nos. 52-111543, 54-160331 and 54-76538). Therefore, such a vacuum spray drier is especially preferred.

The above-mentioned distillation device may be used alone or in combination of two or more of them. For example, in the case when the amount of the waste water to be treated is too large relative to the treatment ability of the device, the waste water can be first concentrated to a level at which its fluidity is maintained by any batch distillation device followed by being subjected to a continuous distillation device so that the cost and the labor for the treatment can be reduced.

According to the process of the present invention, at least about 80% or more, preferably about 90% or more, more preferably about 95% or more and most preferably about 98% or more of phosphorus, determined as TP (i.e., total phosphorus concentration), in the waste water is removed by the distillation step.

As described above, the waste organic solvents generated from the reaction step are generally separated from the waste water. By applying the waste organic solvents to the above-mentioned vacuum spray drier, a high quality of organic solvents can be recovered more easily and economically than conventional recovering procedures using a rectification tower. The recovered organic solvents can be immediately fed into the reaction step so that the amount of the organic solvents to be used can be reduced. As a result, it may be possible to operate the entire process continuously with high productivity substantially without generating deleterious waste water. Such a continuous operation is particularly preferred for industrial use.

Of course, the process of the present invention can be applied to the case in which the waste water generated during production of the halogen-containing phosphate ester is treated separately. That is, the waste water, which is generated during purification of the halogen-containing phosphate ester by crystallization, may be first separated from the solid components and then the separated waste water may be transported to a separate facility and subjected to a intensive cleaning process including a distillation step, instead of carrying out the entire process including the distillation step continuously as mentioned above. Such a separate treatment may be found more effective than the continuous treatment, depending on conditions including the amount of the waste water to be treated.

EXAMPLE

Although a preferred example of the present invention is described below, the scope of the present invention is not intended to be limited to the following example.

In the following example, concentrations of TOC (total organic carbon) materials were determined according to JIS K0102-22.1 (combustion oxidation-infrared TOC analysis), concentrations of COD materials were determined according to JIS K0102-17 (determination of oxygen consumption amount by potassium permanganate at 100° C.) and concentrations of TP (total phosphorus) were determined according to JIS K-0102-46.3.2 (nitric acid-perchloric acid decomposition method).

To a reaction vessel equipped with stirrer, thermometer, dropping funnel, collecting device for hydrochloric acid and condenser, 5775 Kg of tribromoneopentylalcohol and 7500 Kg of o-dichlorobenzene were charged. To the dropping funnel, 900 Kg of phosphorus oxychloride was charged. The mixture of tribromoneopentylalcohol and o-dichlorobenzene was then heated to 100° C.

To the above mixture, 10.5 Kg of anhydrous aluminum chloride was added, followed by gradual addition of the phosphorus oxychloride in the dropping funnel for four hours. After completion of the addition, the reaction was gradually heated to 160° C. for two hours with stirring to complete the reaction. Hydrochloric acid generated during the addition was recycled by the recycling device. The reaction was then treated at a temperature of 110° C. under a pressure of 200 Torr for six hours to give 12774 Kg of a reaction mixture of transparent yellow appearance.

The reaction mixture was then cooled to 65° C., followed by addition of 384 Kg of water (i.e., 3 parts by weight of water was added to 100 parts by weight of the reaction mixture). After stirring thoroughly, the reaction mixture was cooled to near room temperature to give a slurry. The slurry was treated with continuous centrifugal device (High-Speed Decanter Type Z53, Tanabe Willtec Inc.) to separate a waste water, a waste solvent and a cake. The cake was then washed with methanol and dried to give tris(tribromoneopentyl) phosphate as a purified product.

The waste solvent was separated from the waste water by separation and filtration. 442 Kg of the waste water (TOC concentration: 130 mg/L, COD concentration: 100 mg/L, TP concentration: 50.3 mg/L, and pH=1.6) was subjected to continuous distillation. After operation for about one hour, 429 Kg of treated water (TOC concentration: 84 mg/L, COD concentration: 77.3 mg/L, and TP concentration: 0.45 mg/L, and pH=2.2) and 13.2 Kg of distillation residue (white-yellow solid) were obtained.

The type of the device and conditions used in the continuous distillation of the present example are as follows:

vacuum spray drier: , CRUX System Type CRUX-8BB (batch type), Hosokawa Micron Corporation

| conditions: | heat tube temperature | 200° C. |
|---|---|---|
| | collector container temperature | 140° C. |
| | vacuum degree | 100 Torr |

When the recycled waste solvent was treated with the spray drier, recycled solvent was obtained in a recycling rate of 91.1%.

The purified product was obtained at 98.5% yield (5952 Kg). The product had a melting point of 181° C. and hue of solution of Hz=10 (at 10 g of product/50 ml of tetrahydrofuran). The aluminum content in the product was 2 ppm. Analysis with liquid chromatography showed that the purity of the product was 99.8%.

Industrial Applicability

The present invention allows application of a distillation method to treatment of such waste water, which has not been considered to be practical for industrial use. Waste water generated during production of halogen-containing phosphate esters has encountered difficulties in being treated by conventional biodegradation methods. Thus, according to the present invention, the waste water can be easily and effectively treated to be pollutant-free without using any special treatment method such as dilution of waste water and addition of flocculant as used in the conventional biodegradation treatment. In particular, according to the present invention, the waste water generated during industrial-scale production of a halogen-containing phosphate ester can be treated at a relatively low cost with relatively low impact upon the environment. Furthermore, the treated waste water can be directly drained to sewerage or river. Therefore, a halogen-containing phosphate ester can be produced without substantial adverse effects on the living and natural environment.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A process for producing a halogen-containing phosphate ester, comprising the steps of:
   (i) reacting a phosphorus halide selected from the group consisting of phosphorus oxyhalides and phosphorus pentahalides with a halogen-containing hydroxy compound to obtain a reaction mixture including a halogen-containing phosphate ester,
   (ii) purifying the halogen-containing phosphate ester by adding an aqueous medium selected from the group consisting of water, neutral aqueous solutions, acidic aqueous solutions and basic aqueous solutions to the reaction mixture to crystallize the halogen-containing phosphate ester, and
   (iii) distilling waste water after crystallization of the halogen-containing phosphate ester.

2. The process according to claim 1, wherein the melting point of the halogen-containing phosphate ester is about 30° C. or more.

3. The process according to claim 2, wherein the melting point of the halogen-containing phosphate ester is about 90° C. or more.

4. The process according to claim 1, wherein the halogen-containing hydroxy compound is a halogenated aliphatic hydroxy compound.

5. The process according to claim 4, wherein the halogenated aliphatic hydroxy compound is a brominated neopentyl alcohol.

6. The process according to claim 5, wherein the brominated neopentyl alcohol is tribromoneopentyl alcohol.

7. The process according to claim 1, wherein the halogen-containing phosphate ester is tris(tribromoneopentyl) phosphate.

8. The process according to claim 1, wherein about 0.001 to about 20 parts by weight of the aqueous medium is added to 100 parts by weight of the reaction mixture in the purification step.

9. The process according to claim 1, wherein, prior to the step of distillation, the waste water from the purification step is subjected to separation from the halogen-containing phosphate ester by the use of a continuous centrifugal device.

10. The process according to claim 1, wherein the step of distillation is carried out in a continuous manner.

11. A process for treating waste water generated during production of a halogen-containing phosphate ester comprising distilling the waste water after crystallization of the halogen-containing phosphate ester, wherein the halogen-containing phosphate ester has been crystallized by adding an aqueous medium selected from the group consisting of water, neutral aqueous solutions, acidic aqueous solutions and basic aqueous solutions to a reaction mixture, wherein the reaction mixture is obtained by reacting a phosphorous halide selected from the group consisting of phosphorous oxyhalides and phosphorous pentahalides with a halogen-containing hydroxy compound.

12. The process according to claim 1, wherein the step of distillation is carried out using a spray drier.

* * * * *